United States Patent
Bell et al.

(10) Patent No.: US 8,785,207 B2
(45) Date of Patent: Jul. 22, 2014

(54) METHOD AND APPARATUS FOR MEASURING MULTIPLE PARAMETERS IN-SITU OF A SAMPLE COLLECTED FROM ENVIRONMENTAL SYSTEMS

(75) Inventors: Ryan J. Bell, Pinellas Park, FL (US); R. Timothy Short, St. Petersburg, FL (US); Strawn K. Toler, Bradenton, FL (US); Robert H. Byrne, St. Petersburg, FL (US)

(73) Assignee: SRI International, Menlo Park, CA (US)

( * ) Notice: Subject to any disclaimer, the term of this patent is extended or adjusted under 35 U.S.C. 154(b) by 622 days.

(21) Appl. No.: 12/558,381

(22) Filed: Sep. 11, 2009

(65) Prior Publication Data

US 2010/0070201 A1    Mar. 18, 2010

Related U.S. Application Data

(60) Provisional application No. 61/096,690, filed on Sep. 12, 2008.

(51) Int. Cl.
*G01N 33/18* (2006.01)
*G01N 35/08* (2006.01)
*G01N 1/18* (2006.01)

(52) U.S. Cl.
USPC ............ 436/133; 436/43; 436/119; 436/121; 436/146; 436/163; 436/173; 702/24; 73/19.1

(58) Field of Classification Search
USPC .......... 436/43, 119, 121, 133, 146, 163, 173; 702/24; 73/19.1
See application file for complete search history.

(56) References Cited

U.S. PATENT DOCUMENTS

| | | | | |
|---|---|---|---|---|
| 3,664,438 | A | * | 5/1972 | Winget et al. ...................... 175/6 |
| 3,712,481 | A | * | 1/1973 | Harwood ....................... 414/736 |
| 3,930,798 | A | * | 1/1976 | Schierjott et al. ............... 436/62 |
| 4,109,601 | A | * | 8/1978 | Ronnevig ...................... 405/190 |
| 4,754,654 | A | * | 7/1988 | Johnson et al. ............ 73/864.34 |
| 4,845,025 | A | * | 7/1989 | Lary et al. ......................... 435/2 |
| 5,047,212 | A | * | 9/1991 | Blades et al. ............. 422/82.02 |
| 5,341,834 | A | * | 8/1994 | Doherty et al. .......... 137/599.07 |
| 5,356,458 | A | * | 10/1994 | Javadi et al. ..................... 95/13 |
| 5,441,071 | A | * | 8/1995 | Doherty et al. ............ 137/15.05 |
| 5,466,604 | A | * | 11/1995 | Yang et al. ................. 435/286.1 |
| 5,552,319 | A | * | 9/1996 | Yang et al. ................. 435/286.5 |
| 5,643,799 | A | * | 7/1997 | Atwater et al. ............... 436/133 |
| 5,925,572 | A | * | 7/1999 | Byrne et al. .................. 436/163 |
| 5,981,289 | A | * | 11/1999 | Wright et al. ................ 436/121 |
| 6,113,858 | A | * | 9/2000 | Tang et al. ................. 422/82.09 |
| 6,143,246 | A | * | 11/2000 | Lee et al. ......................... 422/62 |

(Continued)

OTHER PUBLICATIONS

Mandernack, K. W. et al, Marine Chemistry 1999, 66, 201-213.*

(Continued)

*Primary Examiner* — Arlen Soderquist

(57) ABSTRACT

The present invention relates generally a method and apparatus for measuring multiple parameters in-situ in a sample collected from an environmental system via a single device. In one embodiment, the method includes collecting the sample from said environmental system via the single device, measuring a first parameter of the sample in-situ via the single device, adding a reagent tot the sample within the single device to create a reagent infused sample and measuring a second parameter of the sample in-situ via the single device using the reagent infused sample.

6 Claims, 7 Drawing Sheets

(56) References Cited

U.S. PATENT DOCUMENTS

| | | | |
|---|---|---|---|
| 6,444,474 B1* | 9/2002 | Thomas et al. | 436/146 |
| 6,561,046 B1* | 5/2003 | Taylor et al. | 73/863.23 |
| 6,564,155 B2* | 5/2003 | Vogel et al. | 702/25 |
| 7,273,561 B1* | 9/2007 | Palmer | 210/742 |
| 7,727,770 B2* | 6/2010 | Byrne et al. | 436/163 |
| 7,842,507 B1* | 11/2010 | Byrne | 436/133 |
| 7,943,391 B1* | 5/2011 | Byrne | 436/163 |
| 8,012,760 B1* | 9/2011 | Byrne | 436/133 |
| 8,071,031 B1* | 12/2011 | Byrne | 422/82.01 |
| 8,077,311 B1* | 12/2011 | Byrne et al. | 356/319 |
| 2002/0001851 A1* | 1/2002 | DeGrandpre | 436/133 |
| 2006/0234389 A1* | 10/2006 | Byrne et al. | 436/163 |
| 2008/0264323 A1* | 10/2008 | Gosling | 114/330 |
| 2010/0064825 A1* | 3/2010 | Bell et al. | 73/863.83 |

OTHER PUBLICATIONS

Johnson, K. S. et al, Analytica Chimica Acta 1986, 179, 245-257.*
LaPack, M. A. et al, Analytical Chemistry 1990, 62, 1265-1271.*
Taylor, C. D. et al, Marine Technology Society Journal 1993, 27, 32-44.*
Andrew, K. N. et al, Analytical Chemistry 1994, 66, 916A-922A.*
Jannasch, H. W. et al, Analytical Chemistry 1994, 66, 3352-3361.*
Daniel, A. et al, Marine Chemistry 1995, 51, 67-77.*
Short, R. T. et al, Measurement Science and Technology 1999, 10, 1195-1201.*
Short, R. T. et al, Journal of the American Society for Mass Spectrometry 2001, 12, 676-682.*
Okamura, K. et al, Marine Chemistry 2001, 76, 17-26.*
Statham, P. J. et al, Journal of the Society for Underwater Technology 2003, 25, 129-134.*
Martz, T. R. et al, Analytical Chemistry 2003, 75, 1844-1850.*
Laes, A. et al, Marine Chemistry 2005, 97, 347-356.*
Statham, P. J. et al, Environmental Science and Technology 2005, 39, 9440-9445.*
Nakano, Y. et al, Journal of Oceanography 2006, 62, 71-81.*
Liu, X. et al, Environmental Science and Technology 2006, 40, 5036-5044.*
Bell, R. J, et al, et al, Environmental Science and Technology 2007, 41, 8123-8128.*
Seidel, M. P. et al, Marine Chemistry 2008, 109, 18-28.*
Lapham, L. L. et al, et al, Environmental Science and Technology 2008, 42, 7368-7373.*
Scarano, E. et al, Analytical Chemistry 1975, 47, 1055-1065.*
Sakamoto-Arnold, C. M. et al, Liminology and Oceanography 1986, 31, 894-900.*
Gamo, T. et al, Analytical Sciences 1994, 10, 843-848.*
Feely, R. A. et al, Deep-Sea Research II 1995, 365-386.*
Saito, H. et al, Deep-Sea Research I 1995, 42, 2025-2033.*
Bates, N. R. et al, Deep-Sea Research II 1996, 43, 347-383.*
DeGrandpre, M. D. et al, Limnology and Oceanography 1997, 42, 21-28.*
McElligott, S. et al, Marine Chemistry 1998, 60, 63-73.*
Wang, J. et al, Analytical Communications 1998, 35, 241-243.*
Tabacco, M. B. et al, Analytical Chemistry 1999, 71, 154-161.*
Wang, J. et al, Fresenius' Journal of Analytical Chemistry 1999, 364, 28-31.*
Luther, III G. W. et al, Environmental Science and Technology 1999, 33, 4352-4356.*
Lueker, T. J. et al, Marine Chemistry 2000, 70, 105-119.*
Le Bris, N. et al, Marine Chemistry 2000, 72, 1-15.*
Stoll, M. H. C. et al, Analytical Chemistry 2001, 73, 4111-4116.*
Byrne, R. H. et al, Analytica Chimica Acta 2002, 451, 221-229.*
Luther, III G. W. et al, "A Continuous Flow Electrochemical Cell for Analysis of Chemical Species and Ions at High Pressure: Laboratory, Shipboard, and Hydrothermal Vent Results" in ACS Symposium Series Environmental Electrochemistry, 2002, Taillefert, M., et al, editors, American Chemical Society: Washington, DC, pp. 54-72.*
Johnson, K. S. et al, Deep Sea Research I 2002, 49, 1291-1305.*
Choi, Y. S. et al, Analytical Chemistry 2002, 74, 2435-2440.*
Faber, E. et al, Journal of Volcanology and Geothermal Research 2003, 125, 13-23.*
Le Bris, N. et al, Deep-Sea Research I 2003, 50, 737-747.*
Watanabe, A. et al, Marine Chemistry 2004, 85, 75-87.*
Wenner, P. G. et al, Trends in Analytical Chemistry 2004, 23, 288-295.*
Chapin, T. P. et al, Analytica Chimica Acta 2005, 543, 199-208.*
Wolf-Gladrow, D. A. et al, Marine Chemistry 2007, 106, 287-300.*
Wang, Z. A. et al, Analytica Chimica Acta 2007, 596, 23-36.*
Herczeg, A. L. et al, Nature 1985, 315, 133-135.*
Millero, F. J. et al, Marine Chemistry 1993, 44, 269-280.*
McElligot, S. et al, Marine Chemistry 1998, 60, 63-73.*
Bandstra, L. et al, Marine Chemistry 2006, 100, 24-38.*
Herczeg, A. L. et al, Geochimica et Cosmochimica Acta 1984, 48, 827-845.*

* cited by examiner

METHOD AND APPARATUS FOR MEASURING MULTIPLE PARAMETERS IN-SITU OF A SAMPLE COLLECTED FROM ENVIRONMENTAL SYSTEMS

CROSS REFERENCE TO RELATED APPLICATIONS

This application claims the benefit of U.S. Provisional Application No. 61/096,690, filed on Sep. 12, 2008, which is herein incorporated by reference in its entirety.

FIELD OF THE INVENTION

The present invention relates generally to underwater sampling of a water column and sediment pore water in seawater or freshwater, and more specifically to a method and apparatus for measuring multiple parameters in-situ of a sample collected from environmental systems.

BACKGROUND OF THE INVENTION

Ocean acidification is a critical issue for the twenty-first century impacting on the health of the ocean, the productivity of fisheries and the conservation and preservation of unique marine environments such as coral reefs. Ocean acidification is an important and potentially dangerous consequence of increasing concentration of anthropogenic carbon dioxide in the Earth's atmosphere. Measurements such as aqueous carbon dioxide partial pressure ($pCO_2$), acidity (pH), total dissolved inorganic carbon (DIC) and total alkalinity (TA) are required to characterize the ocean carbon cycle and such carbon systems.

In anoxic areas (e.g., sediments and stagnant basins) the presence of hydrogen sulfide ($H_2S$) further complicates the carbon system, acting as another component to alkalinity and, thus, affecting the pH and other carbon system parameters. The sulfide system is similar to the carbon system in that it exists in multiple aqueous species ($H_2S$, $H_S^-$, and $S^{-2}$), and the relative abundance of these species is pH dependent. The presence of $H_2S$ contributes to the TA, and thus in order to resolve the carbon system in anoxic areas, a third determination of $H_2S$ must be also made. Further, $H_2S$ is a very reactive chemical that can influence microorganisms that, in turn, influence carbon cycling in aqueous systems.

Devices that sample pore water in sediments require pumps with precisely controlled flow rates, often less than 1 ml/min. Some devices use a variety of piston pumps to draw samples to an analyzer or collection device. However, piston pumps are not dependable to provide a constant flow rate for extended periods of time, especially at low flow rates against varying resistance, and they suffer from pulsation of the flow stream.

Osmotic pumps require no electrical power. They are based on the osmotic pressure differential between seawater and saturated salt solutions. However, osmotic pumps cannot be turned on and off, have extremely low flow rates that cannot be effectively controlled.

In addition, currently used underwater sampling devices cannot perform some analyses in-situ. Rather, the sample must be transported to a remote location for performing further analysis. This leads to the possibility of contamination of the sample or loss of analytes, particularly in the case of highly reactive or volatile species.

SUMMARY OF THE INVENTION

In one embodiment, the present invention is directed towards a method for measuring multiple parameters in-situ in a sample collected from an environmental system via a single device. The method comprises collecting said sample from said environmental system via said single device, measuring a first parameter of said sample in-situ via said single device, adding a reagent to said sample within said single device to create a reagent infused sample and measuring a second parameter of said sample in-situ via said single device using said reagent infused sample.

In one embodiment, the present invention is directed towards a computer-readable medium having stored thereon a plurality of instructions, the plurality of instructions including instructions which, when executed by a processor, cause the processor to perform the steps of a method for measuring multiple parameters in-situ in a sample collected from an environmental system via a single device. The method comprises sampling according to an algorithm to collect one or more samples from the environmental system via said single device, measuring a first parameter of each one of said one or more samples in-situ via said single device, adding a reagent to each one of said one or more samples within said single device to create a reagent infused sample of each one of said one said one or more samples and measuring a second parameter of each one of said one or more samples in-situ via said single device using said reagent infused sample of each one of said one or more samples.

BRIEF DESCRIPTION OF THE DRAWINGS

The teaching of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
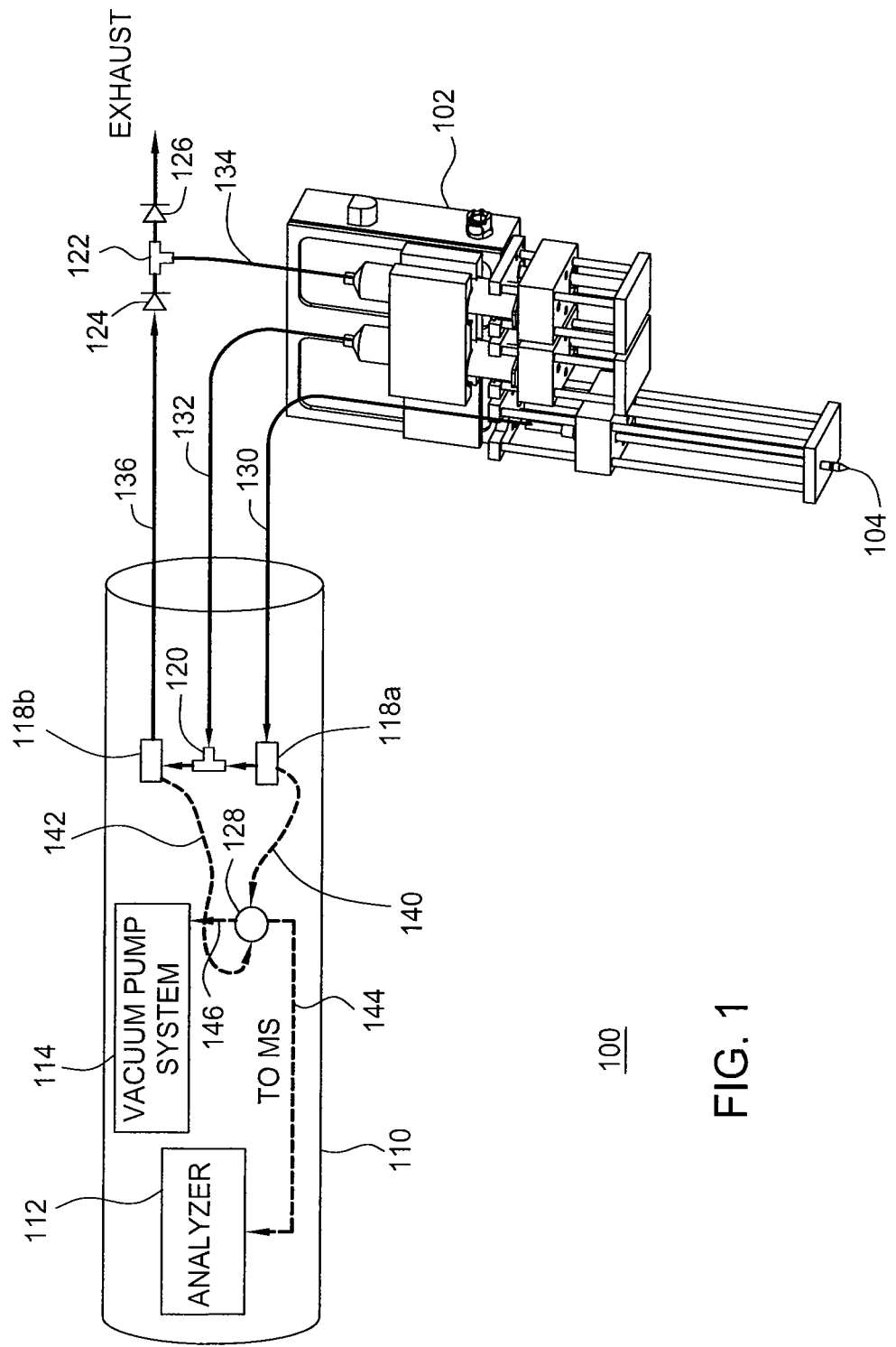
FIG. 1 illustrates a block diagram of one embodiment of a modular underwater sampling apparatus.

The present invention provides a method for directly measuring multiple parameters in-situ of a sample collected from an environmental system using a single device such that all parameters of the environmental system may be calculated. For example, one environmental system in particular is a carbon or carbonate system in seawater.

Ocean acidification is a critical issue for the twenty-first century impacting on the health of the ocean, the productivity of fisheries and the conservation and preservation of unique marine environments such as coral reefs. Ocean acidification is an important and potentially dangerous consequence of increasing concentration of anthropogenic carbon dioxide in the Earth's atmosphere. Measurements such as aqueous carbon dioxide partial pressure ($pCO_2$), pH, total dissolved inorganic carbon (DIC) and total alkalinity (TA) are required to characterize the ocean carbon cycle and such carbon systems.

Generally, at least two of above parameters in a carbon system must be known to constrain the system and obtain all four parameters of $pCO_2$, pH, DIC and TA. Thermodynamic constants $K_x$ and any two measured parameters can be used to calculate all of the parameters in the carbon system.

The amount of gaseous $CO_2$ may be calculated based upon partial pressure measurements of the $CO_2$ in a sample. This measurement is represented as $pCO_2$, as noted above. Generally, this is the simplest parameter to directly measure.

The total amount of inorganic carbon, or DIC, may be measured by completely acidifying the sample. DIC is a useful parameter because it is not a function of temperature or pressure and generally less variable than $pCO_2$ or pH. Traditionally, to measure DIC, the sample must be taken to a remote site. This leads to a potentially inaccurate analysis because the sample can be contaminated or inaccurate due to a loss of analytes, particularly in the case of highly reactive or volatile species. However, the methods provided herein allow the DIC to be measured in-situ without requiring transport of the sample for off-site analysis. Thus, a more accurate measurement and analysis is provided.

Another parameter, TA, can also be measured in situ using the methods and devices disclosed herein. The TA for a sample may be measured by titration of the sample using a known amount of a reagent, for example an acid. Ideally, this is one of the best parameters to measure because it is not affected by gas exchange and is the most orthogonal to other parameters providing the strongest constraint for determining a concentration of carbon, $CO_2$ gas or carbonate ($CO_3^{2-}$) ions and saturation state.

The final parameter, pH, may be calculated by measuring at least two of the above parameters of $pCO_2$, DIC and TA. It is undesirable to directly measure pH and $pCO_2$ as a parameter pair, because pH strongly co-varies with $pCO_2$ and is, therefore, a less ideal second parameter for calculating the other carbon parameters In addition, the methods provided herein can be used to measure the amount of $H_2S$ gas in a sample and a total amount of sulfide in a sample obtained from anoxic areas having a presence of $H_2S$. The amount of $H_2S$ may be measured similar to the way $pCO_2$ is measured and the amount of total dissolved sulfide may be measured similar to the way DIC is measured, as discussed above.

Thus, the present invention provides more accurate calculations of various parameters of the carbon system, e.g., pH, by providing different ways to calculate the various parameters. For example, since only two of the parameters must be measured, one may directly measure DIC and $pCO_2$ to calculate pH or one may directly measure DIC and TA to calculate pH and so forth.

A single device or apparatus for implementing the method for measuring multiple parameters in-situ of a sample collected from an environmental system may be a modular underwater sampling apparatus 100 illustrated in FIG. 1. In other words, the apparatus 100 is a single device for collecting samples from an environmental system and measuring multiple parameters in-situ and not a collection of different independent devices that may be found in a laboratory. Said another way, the apparatus 100 is designed to be a mobile apparatus for in-the-field use.

In one embodiment, the apparatus 100 comprises a sample pump and probe module 102 and an underwater analyzer module 110. The sample pump and probe module 102 includes a sampling probe 104. In one embodiment, the sample pump and probe module 102 may be a syringe pump that can withstand high pressures associated with underwater sampling.

In addition, the sample pump and probe module 102 provides a constant flow to the underwater analyzer module 110. For example, the sample pump and probe module 102 may provide a sample to the underwater analyzer module 110 at a rate of approximately 0.001 milliliters (mL) per minute (min) to 20.0 mL/min. It should be noted that the configuration and specification of the apparatus 100 may be any configuration and specification to provide a sample from the sample pump and probe module 102 to the underwater analyzer module 110 within the above range of flow rate. The flow rate is one factor in determining the accuracy of measurements and analysis performed by the underwater analyzer module 110.

In one embodiment, the underwater analyzer module 110 comprises an analyzer 112, a vacuum pump system 114 and one or more membrane inlet assemblies 118a and 118b. In one embodiment, the analyzer 112 may be a mass spectrometer (MS) analyzer. In one embodiment, the mass spectrometer analyzer may be a linear quadrupole mass filter, e.g., a Transpector 2 Residual Gas Analyzer manufactured by Inficon Inc. of Syracuse, N.Y. It should be noted that other types of analyzers may be used, e.g. analyzers based on ultraviolet-visible (UV-Vis) or infrared (IR) spectroscopy.

In one embodiment, the vacuum pump system 114 may include one or more pumps. For example, a combination of a rough pump and a turbo pump may be used. Alternatively, a single ion pump may be used. It should be noted that any combination or types of pumps may be used to create a vacuum draw and have the ability to exhaust samples in the lines to atmosphere.

In FIG. 1, the solid lines 130, 132, 134 and 136 represent a liquid phase sample flow or line. The dashed lines 140, 142, 144 and 146 represent a gas phase sample flow or line. In one embodiment, the sample may be drawn in via line 130 and fed to a first membrane inlet assembly 118a. The sample may be heated within the first membrane inlet assembly 118a and pervaporated through a semi-permeable membrane into a gas phase. The gas phase sample may then be fed to the analyzer 112 through a switch 128 and lines 140 and 144.

In one embodiment, the vacuum pump system 114 is used to create a vacuum draw within the underwater analyzer module 110. In addition, the vacuum pump system 114 may be used to evacuate the gas phase sample out of lines 140 and 142 when not being analyzed.

The apparatus 100 may provide additional in-situ analysis by providing a reagent (e.g., an acid) via line 132. For example, some determinations such as a measurement of total inorganic carbon or dissolved inorganic carbon (DIC) in a sample require an acidification of the sample. Using the present apparatus 100, one may obtain such measurements in-situ. When the analyzer 112 is ready to perform the analysis, the sample may be fed out of the first membrane inlet assembly 118a to a fluidic tee 120, where the sample is infused with a reagent via the reagent fed by line 132. The reagent infused sample is then fed to a second membrane inlet assembly 118b.

At the second membrane inlet assembly 118b, the reagent infused sample may be pervaporated within the second membrane inlet assembly 118b into a gas phase. The switch or stream selector valve 128 may be positioned to feed the analyzer 112 with the reagent infused sample from the second membrane inlet assembly 118b via lines 142 and 144. As a result, the analyzer 112 may measure a second parameter of the sample using the reagent infused sample.

Thus, using rapid switching between the membrane inlet assemblies 118a and 118b via the switch 128, parameters, such as for example, $pCO_2$, DIC, $H_2S$ and total sulfide can be determined nearly simultaneously. Thus, the single device or apparatus 100 disclosed herein allows for all parameters of an environmental system, anoxic or otherwise, to be measured and calculated in-situ.

Referring back to FIG. 1, an exhaust line is provided within the apparatus 100 to flush the lines. In one embodiment, an exhaust line 136 may run from the second membrane inlet assembly 118b to a first check valve 124, a fluidic tee 122 and a second check valve 126. It should be noted that FIG. 1 illustrates only one possible configuration for a modular underwater sampling apparatus 100.

Figure 3:
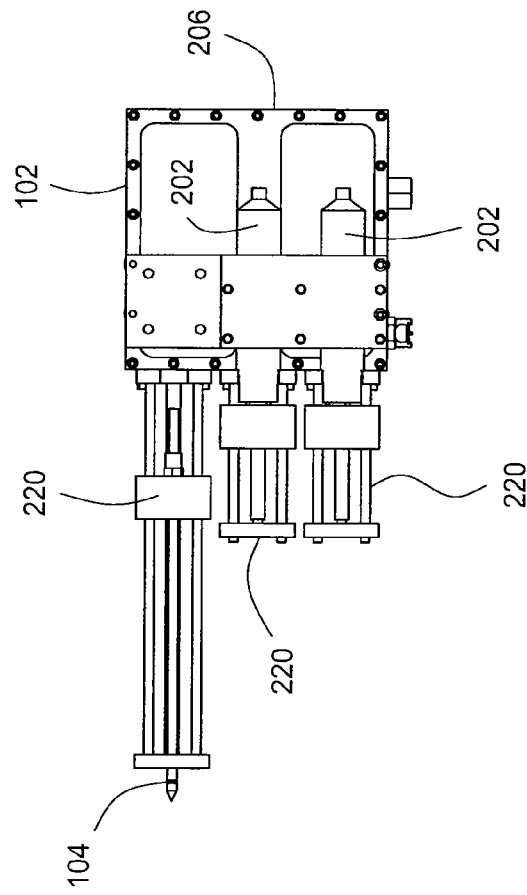
FIG. 3 illustrates a top view of the sample pump and probe of the modular underwater sampling apparatus.
Figure 2:
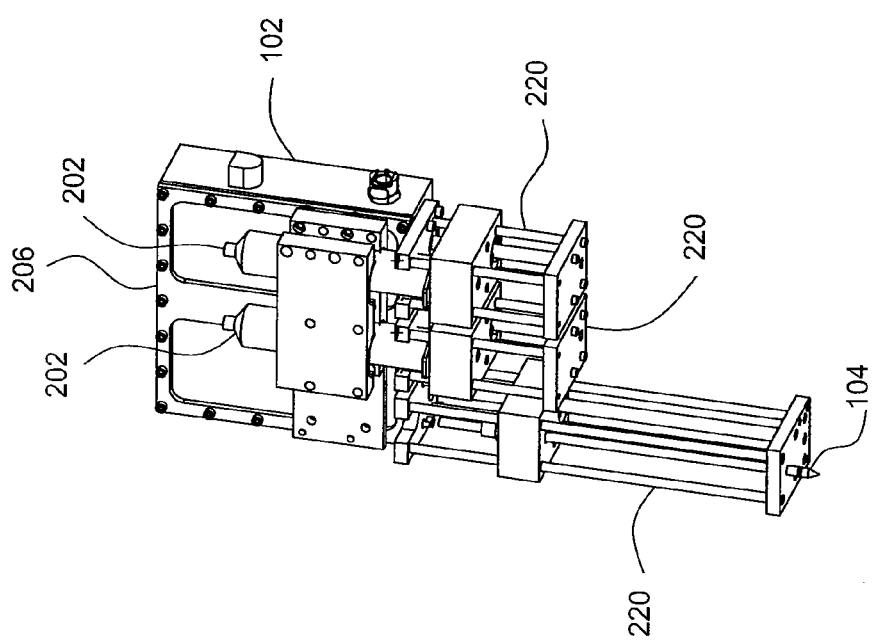
FIG. 2 illustrates an isometric view of a sample pump and probe of the modular underwater sampling apparatus.
Figure 4:
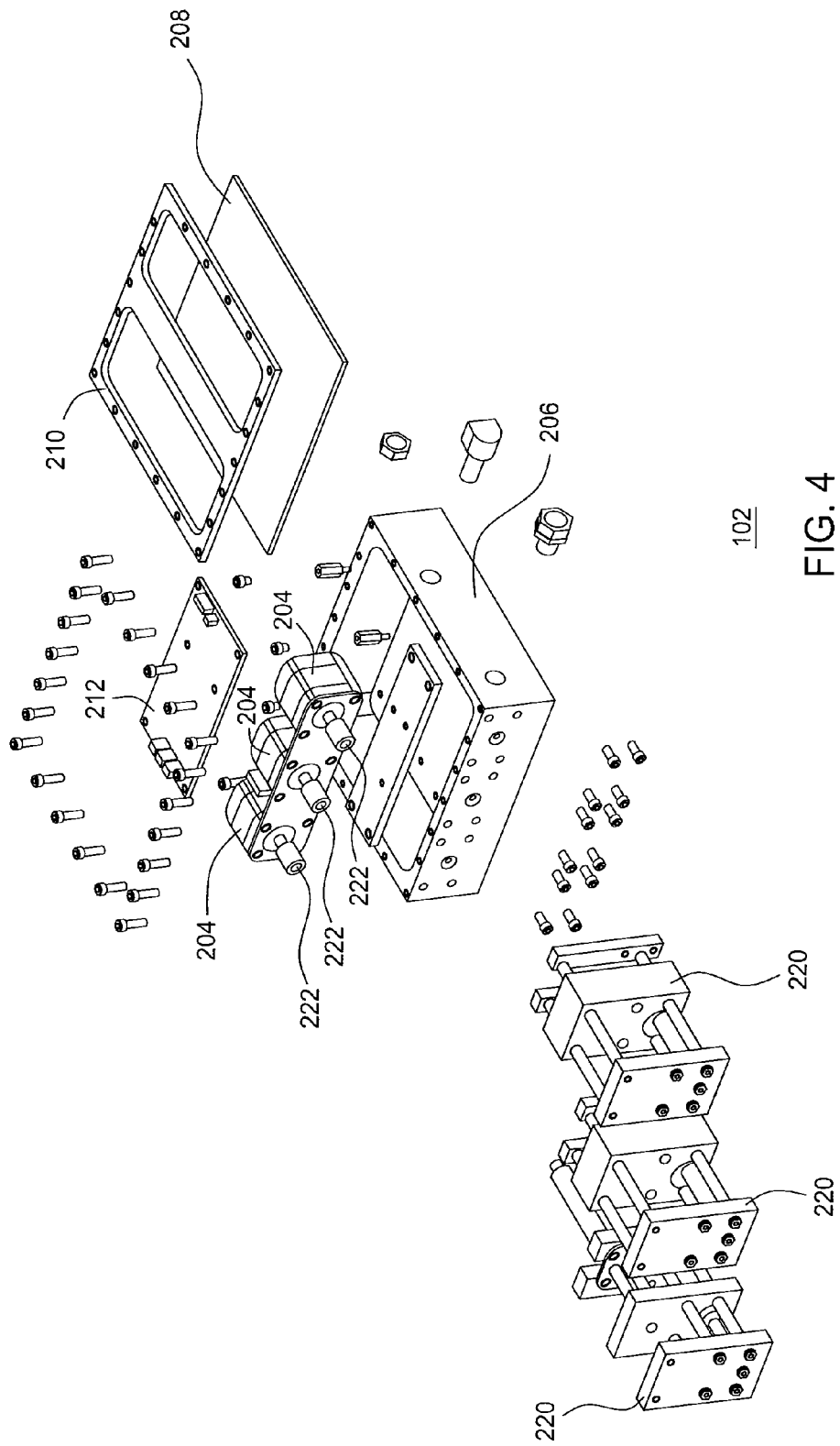
FIG. 4 illustrates an exploded view of the sample pump and probe of the modular underwater sampling apparatus.
Figure 5:
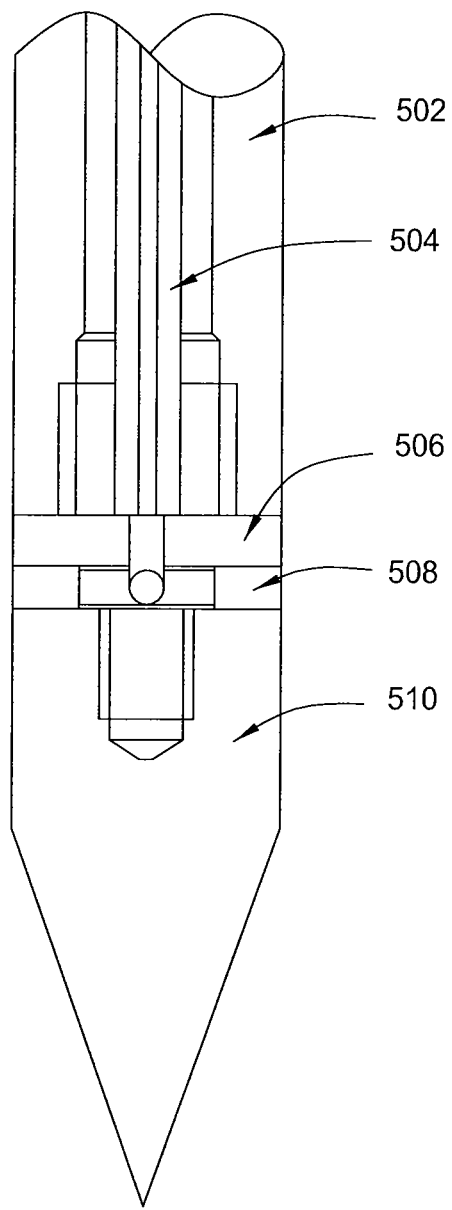
FIG. 5 illustrates a more detailed view of a probe used in the modular underwater sampling apparatus.

FIGS. 2, 3 and 4 illustrate more detailed views of the sample pump and probe module 102. FIG. 2 illustrates an isometric view of a fully assembled sample pump and probe module 102. In one embodiment, the sample pump and probe module 102 comprises a plurality of blocks 220 coupled to an oil filled box 206. The plurality of blocks 220 may be coupled to either a sampling probe 104 or a syringe 202. Notably, the sampling probe 104 and the syringe 202 are interchangeable in any one of the plurality of blocks 220. For example, the sampling probe 104 may replace one of the syringes 202. Any number of or combination of sampling probes 104 or syringes 202 may be used. It should be noted that although three blocks 220 are illustrated, the sample pump and probe module 102 may be fitted with any number of blocks 220 to hold any number of sampling probes 104 or syringes 202 required by a particular application. A more detailed view of the sampling probe 104 is illustrated in FIG. 5 and discussed below. FIG. 3 illustrates a top view of the sample pump and probe module 102.

FIG. 4 illustrates an exploded view of one embodiment of the sample pump and probe module 102. In one embodiment, the sample pump and probe module 102 comprises a plurality of stepper motors 204. The sample pump and probe module 102 may have an equal number of blocks 220 for holding a sampling probe 104 or a syringe 202 and stepper motors 204. Each block 220 is coupled to a stepper motor 204 for operating a sampling probe 104 or a syringe 202. It should be noted that operation of the blocks 220, and correspondingly either a sampling probe 104 or a syringe 202 coupled to a respective block 220, are not limited to a stepper motor 204. Any motor device may be used to operate the blocks 220, such as for example, a direct current (DC) motor.

In operation, motion is transferred via rotating leads 222 on the stepper motors 204 that are sealed by an o-ring. The rotating leads 222 drive a lead screw enabling lateral motion. This lateral motion is used to draw and plunge the blocks 220 to operating the sampling probe 104 or a syringe 202 or precisely control a sampling inlet location.

A printed circuit board (PCB) controller 212 is coupled to the stepper motors 204 and mounted on the oil filled box 206. In one embodiment, the PCB controller 212 is capable of multiple control protocols and used to control the operation of the stepper motors 204 and blocks 220. In one embodiment, the PCB may include a processor, memory and input output devices as described below in FIG. 8.

As a result, the PCB controller 212 may be programmed to implement various sampling algorithms to control the sample probe 104, instruct one of the syringes 202 to provide a reagent for infusing a sample with the reagent to the underwater analyzer module 110 for analysis, and the like. The rotating leads 222 may also be used to operate another motion device, for example a multi-position valve.

In one embodiment, the sampling algorithms may instruct the sampling probe 104 and a corresponding block 220 to collect samples at a predefined schedule. For example, the predefined schedule may include predetermined time intervals (e.g., every second, every minute, every hour, every day, etc.), at predetermined depths (e.g., every centimeter (cm), every 10 cm, every meter (m) etc.) and/or predetermined locations (e.g., 5, different locations, 10 different locations, etc.) on or in the sediment. For example, the algorithm may sample every 10 seconds. Moreover, each sample may be taken 1 centimeter (cm) deeper in the sediment or in different locations. It should be noted that the intervals, depths and locations are provided as examples and that any predetermined time interval and any predetermined depth may be used.

Moreover, using the algorithm and known parameters such as temperature of the water, samples may be collected and analyzed continuously over a period of hours to days. Using the sampling algorithm and the measurements from the analyzer 112, various parameters may be calculated for the environmental system. For example, the calculations may be made for each sample collected in accordance with the predefined schedule. Implementing the sampling algorithms with the methods and the apparatus disclosed herein, very accurate temporal and spatial resolutions may be obtained.

Referring back to FIG. 4, the oil filled box 206 is filled with oil or any other similar liquid. The oil is contained by an oil tolerant flexible sheet 208. The oil tolerant flexible sheet 208 allows ambient hydrostatic pressure to be transferred into the oil, while maintaining a positive overpressure ensuring the impossibility of water entering the system. The oil tolerant flexible sheet 208 is mounted onto the oil filled box 206 with a top cover 210. The components could also be housed inside a hard pressure vessel designed to withstand hydrostatic pressure at depth.

The design of the sample pump and probe module 102 allows the modular underwater sample pump 100 to operate at full ocean depths, e.g., up to 4000 meters (m), where pressure can be greater than 400 atmospheres (atm). Most components are outside of the oil filled box 206 allowing for easy modifications.

Another feature of the design of the sample pump and probe module 102 is that, at most, only coarse filters are required. Currently used designs require filters to be installed to prevent particulates in the sample from interfering with operation of the pumps. The design of the currently disclosed sample pump and probe module 102 provides immunity to particulate or sediment in the sample flow. The stepper motors 204 and drive leads or rotating leads 222 are not in contact with the sample. Rather, the stepper motors 204 simply provide the lateral motion to draw and plunge the syringes 202 or sampling probe 104 in blocks 220. In other words, no precision components are in contact with the flowing sample, hence particulates in the sample will not disrupt or alter sample flow.

In operation, using multiple syringes 202 allows one syringe 202 to draw fluid from a sample point, while a different syringe 202 plunges out a previous sampled fluid to get ready for the next draw. This allows for continuous flow operation. Alternatively, continuous flow operation may be achieved with a single motor 204 via a double action check valve mechanism. It should be noted that the configurations are only provided as examples and not considered limiting. Other configurations are within the scope of the present invention.

Another advantage of using a plurality of syringes 202 is that the sample pump and probe 102 may be used for flow injection analysis (FIA). For example, one of the syringes 202 may be deployed containing a reagent that could be injected into the sample stream. For example, the reagent could be an acid to acidify the sample for measurement of total inorganic carbon or DIC, as noted above with reference to FIG. 1.

FIG. 5 illustrates a more detailed view of one embodiment of the sampling probe 104. The sampling probe 104 is designed to provide millimeter sampling resolution capable of probing environments such as sediments, hydrate environments or vent fluids. These environments have very strong spatial chemical gradients that control the flux of important species including heavy metals, dissolved gases, volatile organic compounds and nutrients. In addition, the sampling probe 104 is designed to provide precision point sampling.

In one embodiment, the sampling probe 104 comprises a support tube 502, a sampling tube 504, a base 506, a sintered frit or disc 508 and a tip 510. The base 506 may hold all the parts together.

The tip 510 is designed with a pointed or angular tip for sediment penetration. In one embodiment, the tip 510 may be a machineable inert material, e.g., polyaryletheretherketone (PEEK), tip. In operation, after the tip 510 is inserted into a sampling point, the sample is drawn to the sintered disc or frit 508. In one embodiment the sintered disc or frit 508 provides a porous disc for sample intake. The sintered disc or frit 508 may be an inert porous material, e.g., a ceramic.

The sintered disc or frit 508 is coupled to the sampling tube 504. In one embodiment, the sampling tube 504 comprises small internal diameter (ID) tubing. The ID of the sampling tube 504 may be approximately 1/64". In one embodiment the sampling tube 504 outer diameter (OD) is approximately 1/16".

In one embodiment, the sampling tube 504 comprises hastelloy C tubing, but could also be titanium or PEEK.

The sampling tube 504 is enclosed in a support tube 502. The support tube 502 may be fabricated from a hard material to protect the sampling tube 504. The ID of the support tube 502 is larger than the OD of the sampling tube 504. For example, if the OD of the sampling tube 504 is approximately 1/16", then the ID of the support tube 502 may be approximately 1/84". It should be noted that the IDs and ODs provided above are examples and that the ODs and IDs may be any length as not introduce an excessive delay in pumping the sample from the sampling probe to the analyzer 112.

Figure 6:
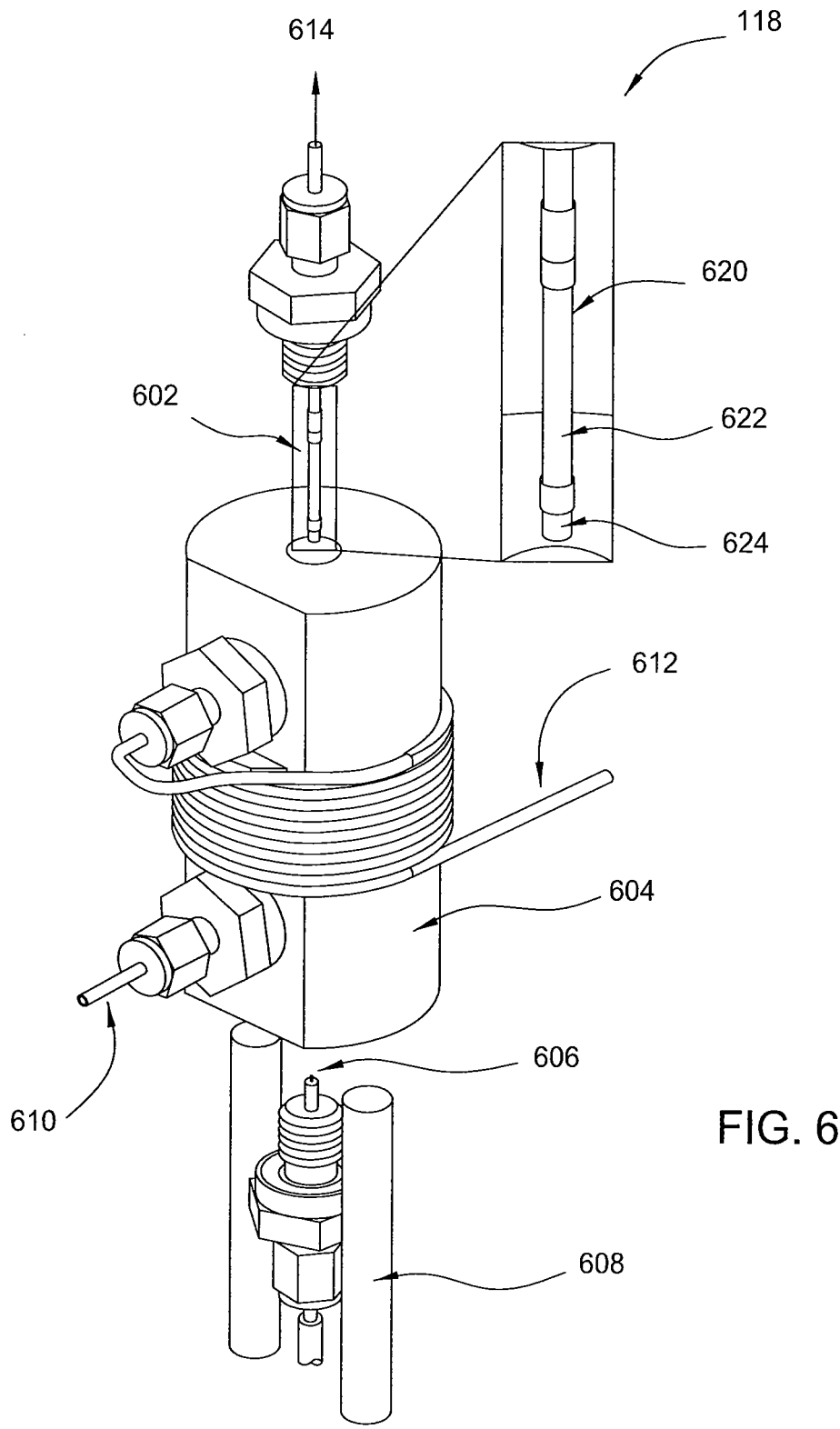
FIG. 6 illustrates a more detailed view of a membrane assembly used in a mass spectrometer module of the underwater sampling apparatus.

FIG. 6 illustrates a more detailed view of the membrane inlet assemblies 118a and 118b (herein collectively membrane inlet assembly 118). In one embodiment, the sample enters the membrane inlet assembly 118 via a sample inlet 612. The sample inlet is wrapped around a heater block 604 that is coupled to a thermocouple 606 and one or more heater cartridges 608.

As discussed above, the sample may be heated within the membrane inlet assembly 118 and pervaporated through a semi-permeable membrane into a gas phase. It should be noted that alternative designs of the modular underwater sampling apparatus 100 contemplate that the sample may be preheated before the sample enters the membrane inlet assembly 118. These alternate design modifications are also within the scope of the present invention. The gas phase sample may then be fed to the analyzer 112 directly or through a switch 128 and lines 140 and 144, as illustrated in FIG. 1.

As discussed above, in one embodiment the vacuum pump system 114 is used to create a vacuum draw in line 614. The vacuum draw 614 pulls the gas phase sample from a membrane interface 602 coupled to or inserted in the heater block 604.

The membrane interface 602 comprises a membrane 620, a sintered rod 622 and a cap 624. In one embodiment, the membrane 620 may comprise a polydimethylsiloxane (PDMS) membrane, the sintered rod 622 may be a porous sintered rod and the cap 624 may comprise a PEEK cap. For example, the PDMS membrane may be mounted in a stretched state on the porous sintered rod. The membrane interface 602 may be sealed with an epoxy or other similar polymer.

The remaining liquid phase sample may be exhausted from the membrane inlet assembly 118 via a sample outlet 610. As illustrated in FIG. 1, the sample outlet 610 may be used to exhaust the sample via line 136 or to carry the sample to fluidic tee 120 for acidification.

Thus, a modular underwater sampling apparatus is described herein. The modular design provides flexibility in easily swapping out the syringe or analyzers for specific applications. For example, the MS analyzer may be easily swapped out for other types of analyzers or optical detectors that relay on other analytical techniques, such as, spectrophotometry, fluorescence and chemiluminescence.

The modular design also isolates multiple fluid connections from sensitive electronic components, such as the MS analyzer. This minimizes potential damage from small water leaks within one or more of the modules.

The additional in-situ analysis provided by the modular underwater sampling allow the modular underwater sampling apparatus to be used for all aspects of aqueous studies, such as for example, vertical and horizontal mapping of chemical distribution, long term observations of chemical variability and deep sea studies.

The design of the modular underwater sampling apparatus provides ability to take samples at deep ocean depths, e.g., up to 4000 m depths, without degradation of pump performance due to increase in hydrostatic pressure. In other words, the present module underwater sampling apparatus is able to withstand the high ambient pressures at extreme ocean depths. Furthermore, the design of the modular underwater sampling apparatus allows for extended continuous operation, providing sufficient power is available.

In addition, the design of the disclosed modular underwater sampling apparatus provides flexibility in use in applications outside of underwater analysis. For example, the modular underwater sampling apparatus may be used in industrial process control or effluent monitoring.

Figure 7:
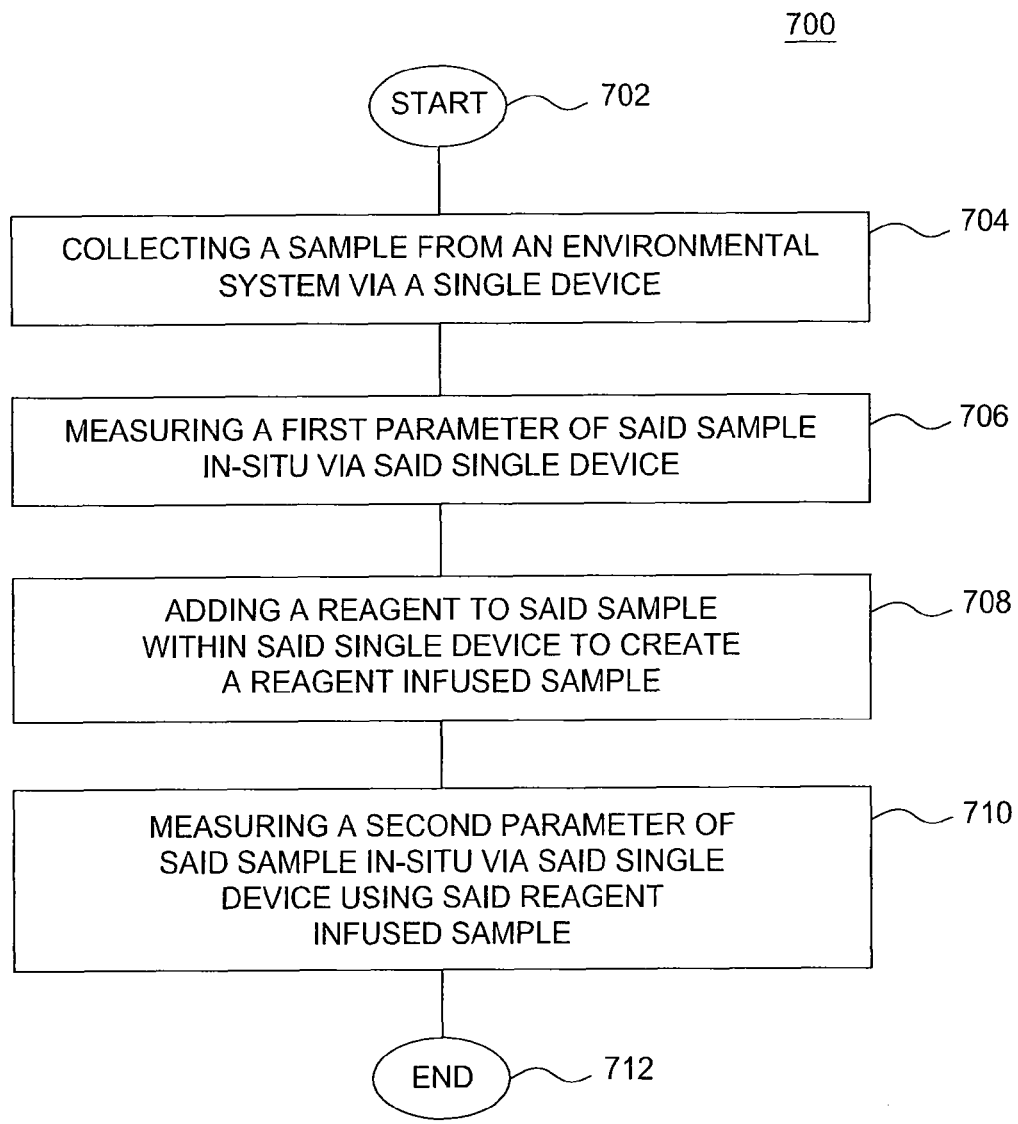
FIG. 7 illustrates a flow chart for one embodiment of a method for measuring parameters in a sample collected from an environmental system via a single device.

FIG. 7 illustrates a flow chart for one embodiment of a method 700 for measuring parameters in a sample collected from an environmental system via a single device. In one embodiment, the single device may be the modular underwater sampling apparatus 100 described above. In one embodiment, the environmental system may be a carbon system, an $H_2S$ system or a carbon system that contains $H_2S$. Moreover, the environmental system may be underwater.

The method 700 begins at step 702. At step 704, the method 700 collects a sample from the environmental system via a single device. As noted above, in one embodiment the single device may be the modular underwater sampling apparatus 100 described above with reference to FIGS. 1-6. The sample may be collected from a body of liquid or sediment in seawater or fresh water.

At step 706, the method 700 measures a first parameter of the sample in-situ via the single device. In one embodiment, depending on the type of environmental system that is sampled, the first parameter may be $pCO_2$ for a carbon system or the amount of dissolved H$_2$S gas in the sample for a H$_2$S system. However, it should be noted that the first parameter may be any one of the parameters discussed above within a carbon system or a H$_2$S system.

At step 708, the method 700 adds a reagent to the sample within the single device to create a reagent infused sample. For example, the reagent may be an acid. The sample may be acidified to measure DIC or TA in carbon systems or total sulfide in H$_2$S systems.

Notably, the method of the present invention measures multiple parameters of an environmental system in-situ. That is, the sample does not have to be sent off-site to be analyzed. This prevents both sample contamination and loss of analytes during transportation of the sample. This provides more accurate measurement and calculation of environmental system parameters.

At step 710, the method 700 measures a second parameter of the sample in-situ via the single device using the reagent infused sample. For example, the second parameter may be DIC or TA for carbon systems or total sulfide in H$_2$S systems. To measure the second parameter, using the apparatus 100, the sample may be acidified in-situ such that the acidified sample may be analyzed and a second parameter, such as DIC or TA for example, may be measured.

Optionally (not shown in FIG. 7), using the measured parameters of the environmental system, the method 700 may further calculate one or more additional parameters in the environmental system, such as pH. Moreover, the method has the capability to measure many different parameters in the environmental system. As discussed above, some environmental systems, such as carbon systems, only require the measurement of two parameters to constrain the system. Thus, the present method provides multiple ways of calculating additional or remaining parameters, such as pH, because different combinations of two measured parameters may be used. This ensures system performance through multiple internal agreement checks. The method 700 ends at step 712.

Figure 8:
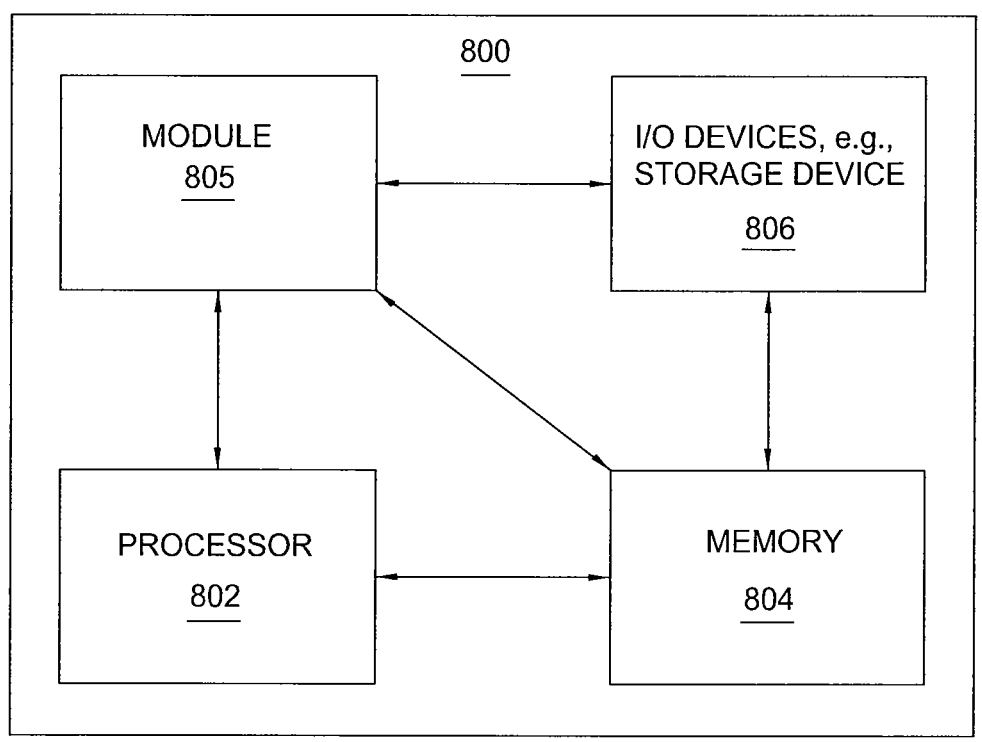
FIG. 8 illustrates a high-level block diagram of a general-purpose computer suitable for use in performing the functions described herein.

FIG. 8 depicts a high-level block diagram of a general-purpose computer suitable for use in performing the functions described herein. In one embodiment, the system 800 may be implemented as the PCB 212, as discussed above, or in a general purpose computer remotely located from the apparatus 100 and in communication with the PCB 212.

As depicted in FIG. 8, the system 800 comprises a processor element 802 (e.g., a CPU), a memory 804, e.g., random access memory (RAM) and/or read only memory (ROM), a module 805 for providing a sampling algorithm, and various input/output devices 806 (e.g., storage devices, including but not limited to, a tape drive, a floppy drive, a hard disk drive or a compact disk drive, a receiver, a transmitter, a speaker, a display, a speech synthesizer, an output port, and a user input device (such as a keyboard, a keypad, a mouse, and the like)).

It should be noted that the present invention can be implemented in software and/or in a combination of software and hardware, e.g., using application specific integrated circuits (ASIC), a general purpose computer or any other hardware equivalents. In one embodiment, the present module or process 805 for providing a sampling algorithm can be loaded into memory 804 and executed by processor 802 to implement the functions as discussed above. As such, the present module or process 805 for providing a sampling algorithm of the present invention can be stored on a computer readable storage medium, e.g., RAM memory, magnetic or optical drive or diskette and the like.

While various embodiments have been described above, it should be understood that they have been presented by way of example only, and should not be considered limiting. Thus, the breadth and scope of a preferred embodiment should not be limited by any of the above-described exemplary embodiments, but should be defined only in accordance with the following claims and their equivalents.

What is claimed is:

1. A method for measuring multiple parameters in-situ in a sample collected from an environmental system via a single device, comprising:
   receiving a constant flow of said sample at a mass spectrometer of said single device from a syringe pump of said single device;
   heating a first portion of said sample within a first membrane inlet assembly coupled to said syringe pump to pervaporate said sample through a semi-permeable membrane into a gas phase of said first portion of said sample;
   measuring, via said mass spectrometer within said single device, a total carbon dioxide gas dissolved (pCO$_2$) in said gas phase of said sample for a carbon system in-situ via said single device;
   feeding a second portion of said sample out of said first membrane inlet assembly via a fluidic tee positioned between said first membrane inlet assembly and a second membrane inlet assembly;
   adding a reagent to said second portion of said sample within said single device to create a reagent infused sample;
   heating said reagent infused sample to pervaporate said reagent infused sample within said second membrane inlet assembly into a gas phase of said reagent infused sample;
   switching a stream selector valve coupled to said first membrane inlet assembly, said second membrane inlet and said mass spectrometer to feed said mass spectrometer with said gas phase of said reagent infused sample;
   measuring a total inorganic carbon (DIC) or a total alkalinity (TA) in said sample for said carbon system in-situ via said mass spectrometer within said single device using said reagent infused sample; and
   calculating a pH of said environmental system using the pCO$_2$ that is measured and the DIC or the TA that is measured.

2. The method of claim 1, wherein said reagent is an acid.

3. The method of claim 1, wherein said single device comprises an apparatus for obtaining a sample underwater, wherein said apparatus comprises:
   said syringe pump comprising a plurality of blocks, at least one syringe coupled to at least one of said plurality of blocks and said at least one sampling probe coupled to a different at least one of said plurality of blocks for collecting said sample underwater.

4. A computer-readable medium storing a plurality of instructions, which when executed by a processor, cause the processor to perform operations for measuring multiple parameters in-situ in a sample collected from an environmental system via a single device, the operations comprising:
   receiving a constant flow of said sample at a mass spectrometer of said single device from a syringe pump of said single device;
   heating a first portion of said sample within a first membrane inlet assembly coupled to said syringe pump to pervaporate said sample through a semi-permeable membrane into a gas phase of said first portion of said sample;

measuring, via said mass spectrometer within said single device, a total carbon dioxide gas dissolved ($pCO_2$) in said gas phase of said sample for a carbon system in-situ via said single device;

feeding a second portion of said sample out of said first membrane inlet assembly via a fluidic tee positioned between said first membrane inlet assembly and a second membrane inlet assembly;

adding a reagent to said second portion of said sample within said single device to create a reagent infused sample;

heating said reagent infused sample to pervaporate said reagent infused sample within said second membrane inlet assembly into a gas phase of said reagent infused sample;

switching a stream selector valve coupled to said first membrane inlet assembly, said second membrane inlet and said mass spectrometer to feed said mass spectrometer with said gas phase of said reagent infused sample;

measuring a total inorganic carbon (DIC) or a total alkalinity (TA) in said sample for said carbon system in-situ via said mass spectrometer within said single device using said reagent infused sample; and calculating a pH of said environmental system using the $pCO_2$ that is measured and the DIC or the TA that is measured.

5. The computer readable medium of claim 4, wherein said algorithm samples continuously.

6. The computer readable medium of claim 4, wherein said algorithm samples at a predetermined interval and at one or more predetermined depths.

* * * * *